US012181685B1

(12) United States Patent
Gu

(10) Patent No.: US 12,181,685 B1
(45) Date of Patent: Dec. 31, 2024

(54) VR MASK AND MASK BRACKET

(71) Applicant: Shenzhen Xinlianyoupin Technology Co., Ltd., Shenzhen (CN)

(72) Inventor: Jinxin Gu, Shenzhen (CN)

( * ) Notice: Subject to any disclaimer, the term of this patent is extended or adjusted under 35 U.S.C. 154(b) by 0 days.

(21) Appl. No.: 18/499,180

(22) Filed: Oct. 31, 2023

(30) Foreign Application Priority Data

Oct. 17, 2023 (CN) .......................... 202322779827.4

(51) Int. Cl.
| | | |
|---|---|---|
| *G02B 27/01* | (2006.01) | |
| *A61F 9/02* | (2006.01) | |
| *B32B 5/24* | (2006.01) | |
| *B32B 27/06* | (2006.01) | |
| *B32B 27/30* | (2006.01) | |

(52) U.S. Cl.
CPC ............ *G02B 27/0176* (2013.01); *A61F 9/02* (2013.01); *B32B 5/245* (2013.01); *B32B 27/065* (2013.01); *B32B 27/304* (2013.01); *B32B 2266/12* (2016.11)

(58) Field of Classification Search
CPC ........ G02B 27/0176; G02B 7/02; G02B 7/12; G02B 7/023; G02B 7/026; G02B 25/00; G02B 25/001; G02B 27/01; G02B 27/017; G02B 27/0172; G02B 2027/0154; B32B 5/245; B32B 27/065; B32B 27/304; B32B 2266/12; B32B 5/24; B32B 27/06; B32B 27/30; A61F 9/02; A61F 9/026; A61F 9/028
USPC ................... 359/480, 481, 13, 630–633, 815
See application file for complete search history.

(56) References Cited

U.S. PATENT DOCUMENTS

| | | | | |
|---|---|---|---|---|
| 2019/0166935 A1* | 6/2019 | Chiang | ................... | B32B 27/12 |
| 2023/0157387 A1* | 5/2023 | Wang | ..................... | B29C 44/14 |
| | | | | 2/9 |

FOREIGN PATENT DOCUMENTS

| | | | | |
|---|---|---|---|---|
| CN | 115202051 B | * | 9/2023 | |
| JP | 2020192337 A | * | 12/2020 | ............. A61B 5/107 |

OTHER PUBLICATIONS

Machine Translation of CN115202051 (Year: 2023).*
Machine translation of JP2020192337 (Year: 2020).*

* cited by examiner

*Primary Examiner* — Jie Lei

(57) ABSTRACT

The present disclosure provides a VR mask and a mask bracket. The VR mask includes a mask main body, which is configured to be connected with a mask bracket. The mask main body includes a fabric layer and a bracket connecting component. The fabric layer is connected to the bracket connecting component to form an accommodating cavity. A filling layer is arranged in the accommodating cavity. When a user wears VR equipment, the fabric layer of the mask main body is in direct contact with the skin of the user. A fabric used in the fabric layer is softer and more comfortable than a hard or viscous material, which can better adapt to the facial contour of the user. Furthermore, the fabric usually has good breathability, which allows air circulation, reduces moisture and excessive sweating, and can satisfy the best performance and improve the wearing experience of the user.

6 Claims, 4 Drawing Sheets

VR MASK AND MASK BRACKET

CROSS-REFERENCE TO RELATED APPLICATIONS

The application claims priority of Chinese patent application CN2023227798274, filed on Oct. 17, 2023, which is incorporated herein by reference in its entireties.

TECHNICAL FIELD

The present disclosure relates to the field of Virtual Reality (VR) accessories, and particularly, to a VR mask and a mask bracket.

BACKGROUND

A Virtual Reality (VR) technology has been widely applied in fields such as entertainment, training, and medical treatment. As an important component of VR equipment, a VR mask is crucial for the comfortableness and the user experience. The traditional VR mask is usually made of an ordinary silica gel material or an ordinary sponge material. These materials may cause discomfort when people wear the VR mask. A user easily feels stiflingly hot and uncomfortable especially when using the VR mask for a long time. Therefore, there is an urgent need for a novel VR mask design to provide a better wearing experience.

SUMMARY

In order to overcome the shortcomings of the prior art, the present disclosure provides a Virtual Reality (VR) mask and a mask bracket, which can improve the wearing experience of the user.

The technical solution adopted by the present disclosure to solve the technical problem is as follows:

The present disclosure provides a Virtual Reality (VR) mask, including a mask main body, wherein the mask main body is configured to be connected with a mask bracket; the mask main body includes a fabric layer and a bracket connecting component; the fabric layer is connected to the bracket connecting component to form an accommodating cavity; and a filling layer is arranged in the accommodating cavity.

As the improvement of the present disclosure, the fabric layer is an ice silk fabric layer.

As the improvement of the present disclosure, the bracket connecting component is a polyvinyl chloride (PVC) connecting plate.

As the improvement of the present disclosure, the ice silk fabric layer is connected to the PVC connecting plate through hot press molding.

As the improvement of the present disclosure, the filling layer includes a first filler and a second filler; the first filler is located on one side close to the PVC connecting plate; and the second filler is located on the other side of the first filler away from the PVC connecting plate.

As the improvement of the present disclosure, the first filler is a memory sponge, and the second filler is gel.

As the improvement of the present disclosure, the mask main body is further provided with a connecting piece connected to the mask bracket, and the connecting piece is located on a lower surface of the PVC connecting plate.

As the improvement of the present disclosure, the connecting piece is a flannel layer, and the flannel layer is connected to the PVC connecting plate through an adhesive or by hot melting.

As the improvement of the present disclosure, a height of the memory sponge is 14-16 mm; a height of the gel is 2.5-3.5 mm; and a width of the mask bracket is 165 mm.

As the improvement of the present disclosure, the ice silk fabric layer is an elastic flexible fabric layer.

As the improvement of the present disclosure, the ice silk fabric layer includes at least one of a polyester fiber, a viscose fiber, polyester or spandex, chinlon or modal, or a cotton blended material.

The present disclosure also provides a VR mask and mask bracket, including a mask bracket, wherein the mask bracket is provided with a viewing port; a mask main body, wherein the mask main body is configured to be connected with the mask bracket; the mask main body is arranged around the viewing port; the mask main body includes a fabric layer and a bracket connecting component; the fabric layer is connected to the bracket connecting component to form an accommodating cavity; and a filling layer is arranged in the accommodating cavity.

As the improvement of the present disclosure, the fabric layer is an ice silk fabric layer.

As the improvement of the present disclosure, the bracket connecting component is a PVC connecting plate.

As the improvement of the present disclosure, the ice silk fabric layer is connected to the PVC connecting plate through hot press molding.

As the improvement of the present disclosure, the filling layer includes a first filler and a second filler; the first filler is located on one side close to the PVC connecting plate; the second filler is located on the other side of the first filler away from the PVC connecting plate; the first filler is memory sponge; and the second filler is gel.

As the improvement of the present disclosure, the mask main body is further provided with a connecting piece, and the mask bracket is provided with a connecting matching member.

As the improvement of the present disclosure, the connecting piece is located on a lower surface of the PVC connecting plate; the connecting matching member is located on an upper surface of an inner side of the mask bracket; the connecting piece is a flannel layer, and the flannel layer is connected to the PVC connecting plate through an adhesive or by hot melting; and the connecting matching member is a hook surface of a hook-and-loop fastener.

As the improvement of the present disclosure, a height of the memory sponge is 14-16 mm; a height of the gel is 2.5-3.5 mm; and a width of the mask bracket is 165 mm.

As the improvement of the present disclosure, the ice silk fabric layer is an elastic flexible fabric layer; the ice silk fabric layer includes at least one of a polyester fiber, a viscose fiber, polyester or spandex, chinlon or modal, or a cotton blended material.

Beneficial effects of the present disclosure are as follows: The present disclosure provides a VR mask. The VR mask includes a mask main body. The mask main body is configured to be connected with a mask bracket. The mask main body includes a fabric layer and a bracket connecting component; the fabric layer is connected to the bracket connecting component to form an accommodating cavity; and a filling layer is arranged in the accommodating cavity. When a user wears VR equipment, the fabric layer of the mask main body is in direct contact with the skin of the user. A fabric used in the fabric layer is softer and more comfortable than a hard or viscous material, which can better adapt to the facial contour of the user. Furthermore, the fabric usually has good breathability, which allows air circulation, reduces moisture and excessive sweating, and can satisfy the best performance and improve the wearing experience of the user.

BRIEF DESCRIPTION OF THE DRAWINGS

In order to explain the technical solutions of the embodiments of the present disclosure more clearly, the following will briefly introduce the accompanying drawings used in the embodiments. The drawings in the following description are only some embodiments of the present disclosure. Those of ordinary skill in the art can obtain other drawings based on these drawings without creative work.

The present disclosure is further described below in detail in combination with the accompanying drawings and embodiments.

DETAILED DESCRIPTION OF THE EMBODIMENTS

Figure 1:
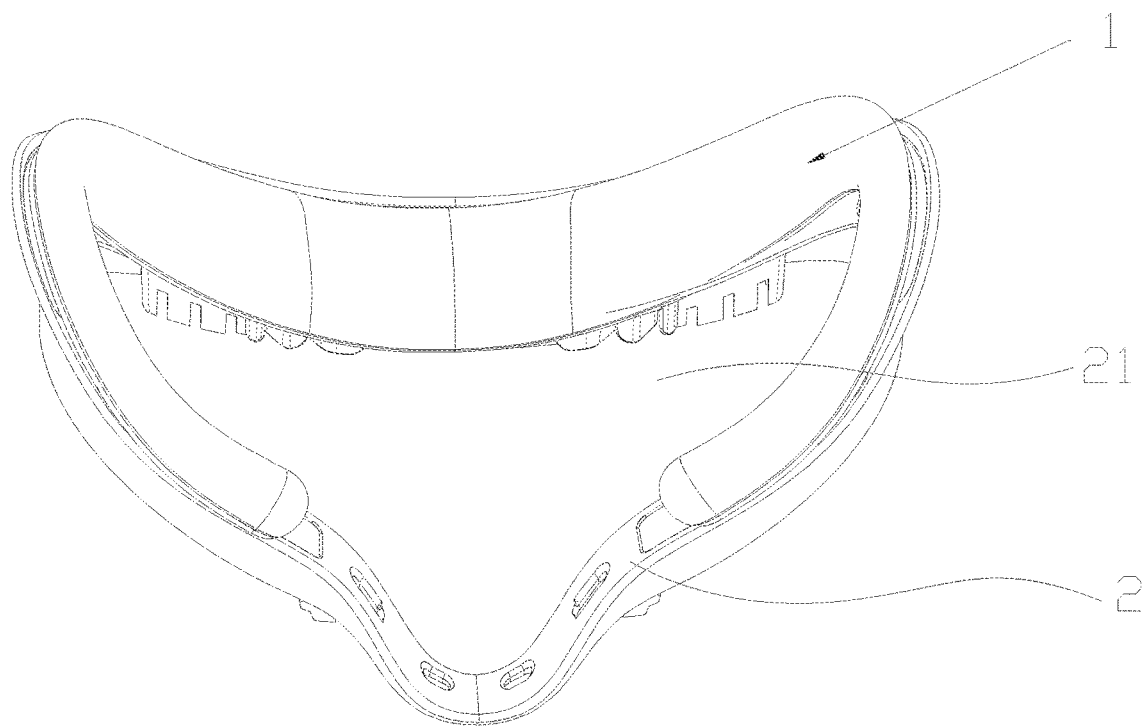
FIG. 1 is a schematic diagram of an entire structure of a mask main body and a mask bracket according to the present disclosure.
Figure 2:
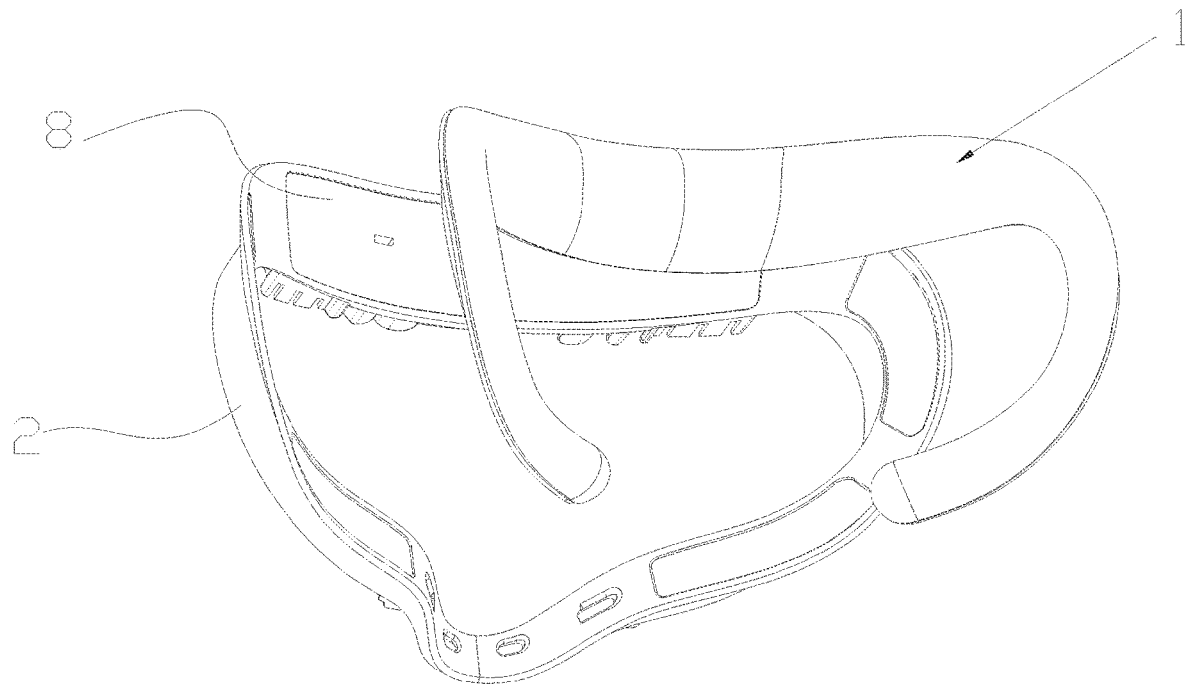
FIG. 2 is an exploded view of a mask main body and a mask bracket according to the present disclosure.
Figure 3:
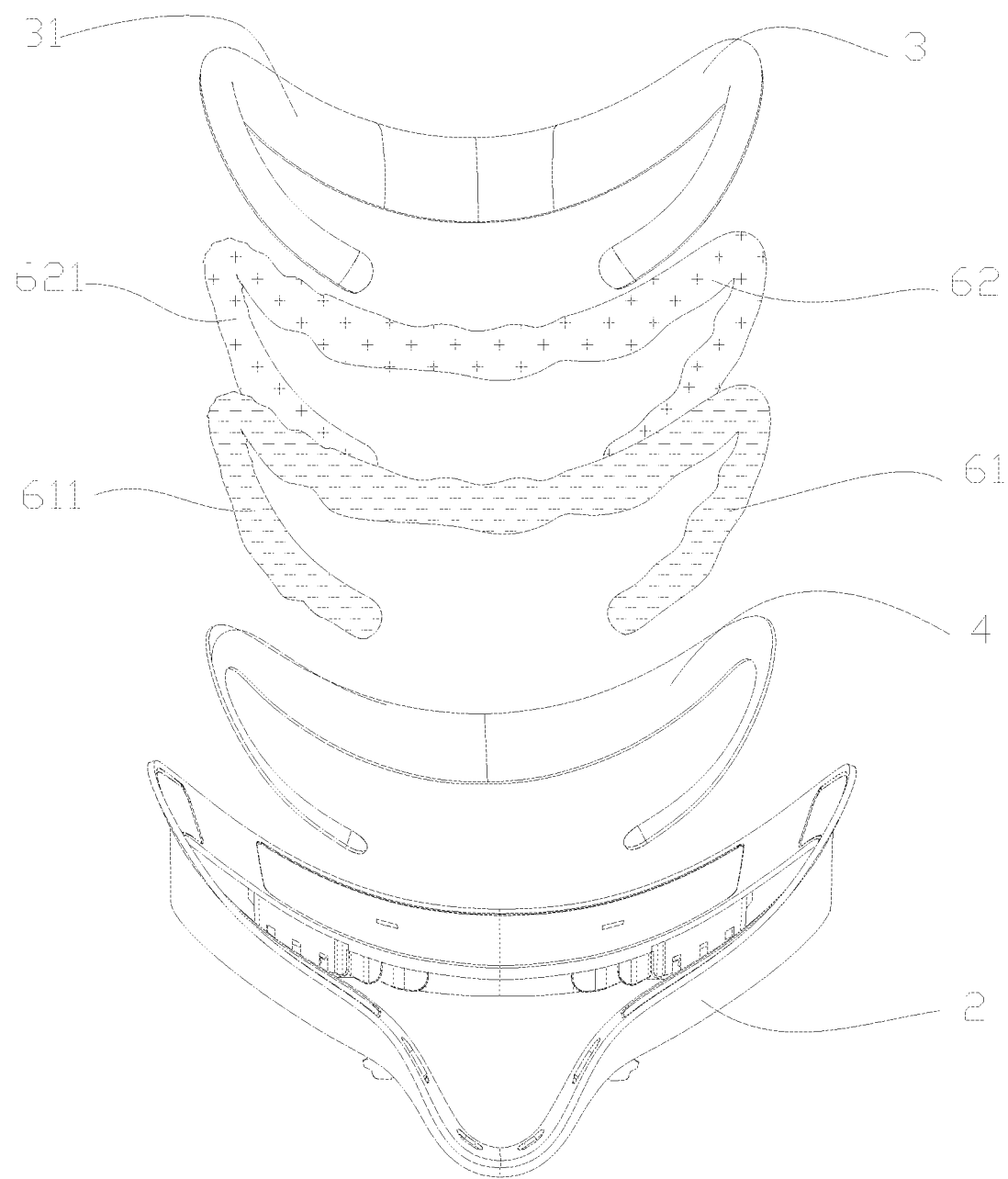
FIG. 3 is another exploded view of a mask main body and a mask bracket according to the present disclosure.
Figure 4:
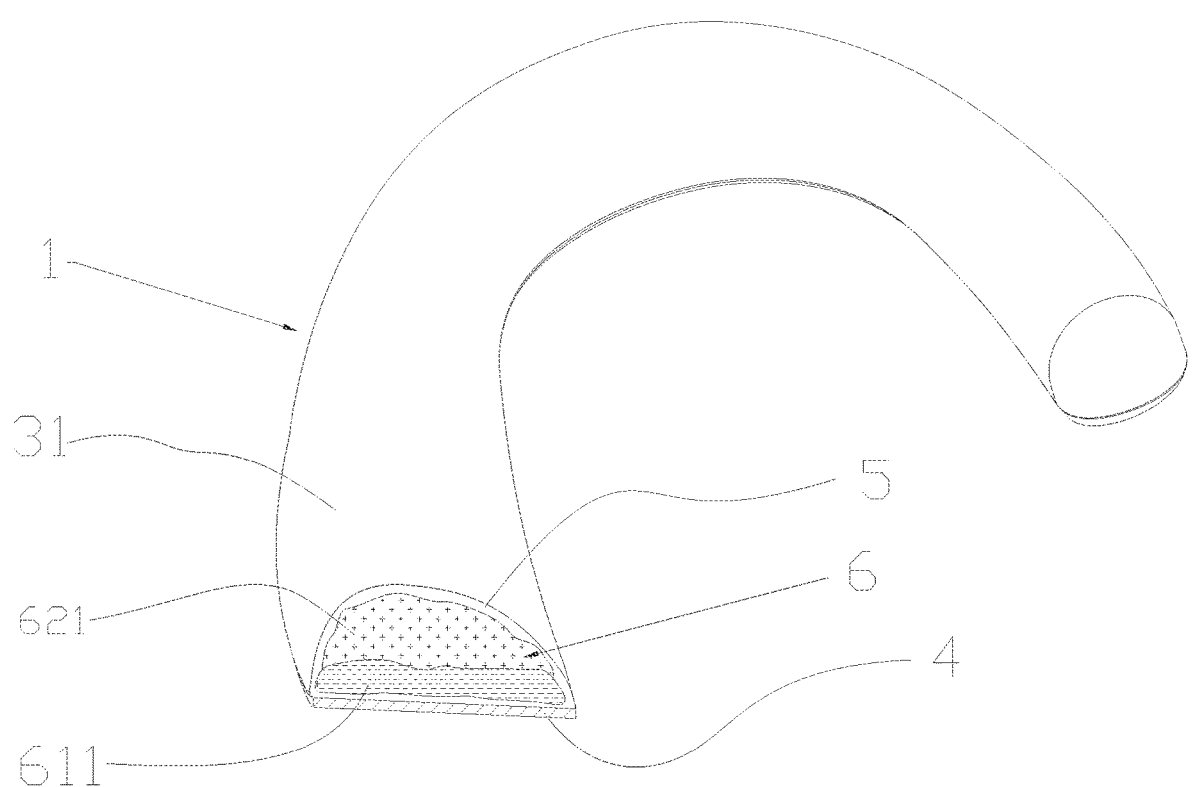
FIG. 4 is a sectional view cut away along a mask main body.
Figure 5:
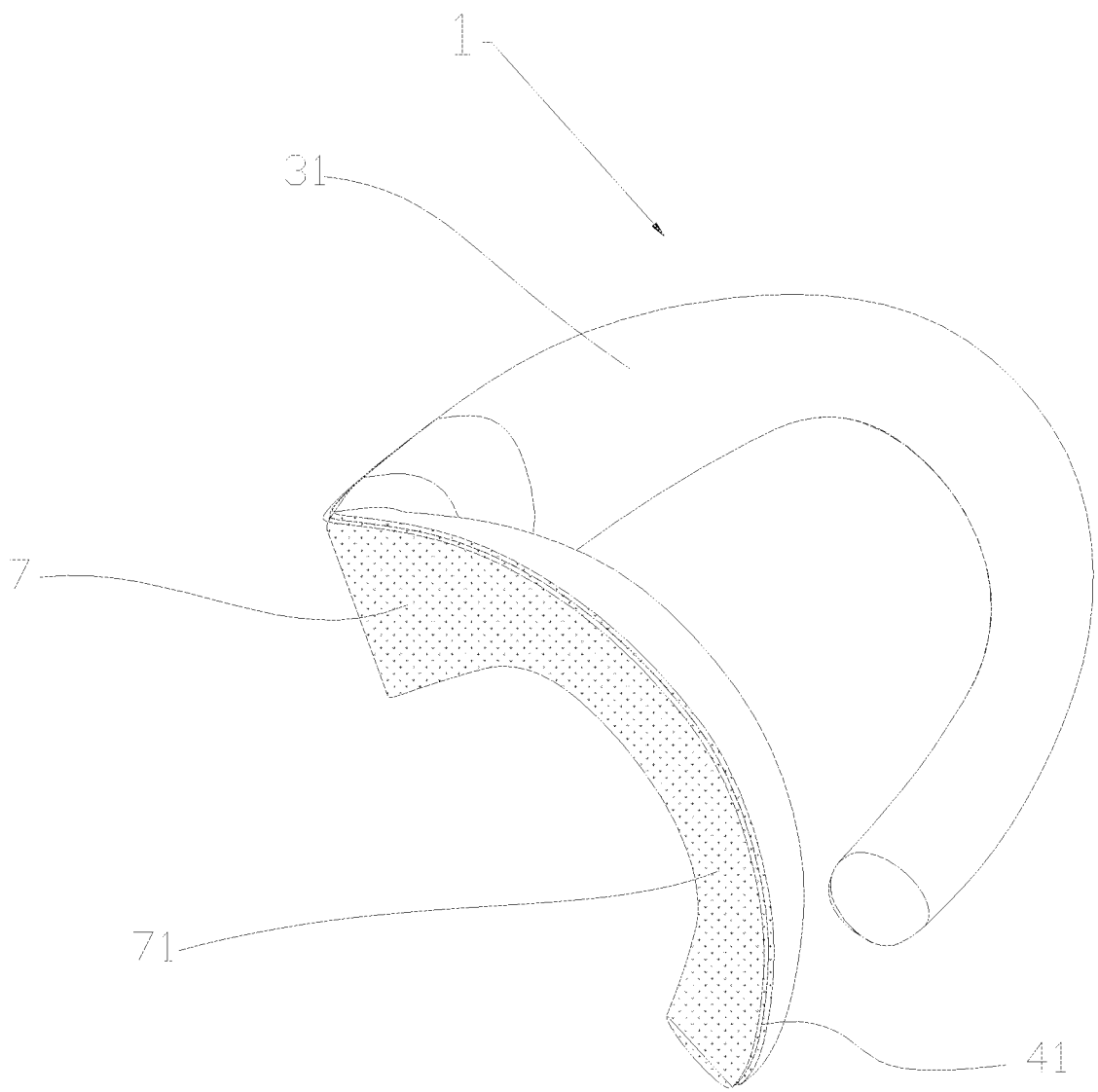
FIG. 5 is a schematic structural diagram of a mask main body according to the present disclosure.

Referring to FIG. 1 to FIG. 5, a VR mask includes a mask main body 1. The mask main body 1 is configured to be connected with a mask bracket 2. The mask main body 1 includes a fabric layer 3 and a bracket connecting component 4; the fabric layer 3 is connected to the bracket connecting component 4 to form an accommodating cavity 5; and a filling layer 6 is arranged in the accommodating cavity 5. Through the above structure, when a user wears VR equipment, the fabric layer 3 of the mask main body 1 is in direct contact with the skin of the user. A fabric used in the fabric layer 3 is softer and more comfortable than a hard or viscous material, which can better adapt to the facial contour of the user. Furthermore, the fabric usually has good breathability, which allows air circulation, reduces moisture and excessive sweating, and can satisfy the best performance and improve the wearing experience of the user.

In this embodiment, the fabric layer 3 is an ice silk fabric layer 31. The ice silk fabric layer 31 is an elastic flexible fabric layer 3; and the ice silk fabric layer 31 includes at least one of a polyester fiber, a viscose fiber, polyester or spandex, chinlon or modal, or a cotton blended material. Through the above structure, an ice silk fabric is known for its cool and comfortable tactile impression. It has the characteristics of moisture absorption and heat dissipation and can effectively keep the skin dry, reduce discomfort and sweating, help air circulation, reduce heat accumulation and moisture. This is very important for a user who wears the VR equipment for a long time, and provides better comfort and freshness for the user. Furthermore, due to its elasticity, the elastic ice silk fabric can better adapt to the facial contour of the user, so as to provide a better-fitted wearing experience, so that the mask can uniformly abut against the face and reduce discomfort, pressure points, and friction. Moreover, the elastic ice silk fabric has a recovery capability, which can be recovered to an original shape quickly after stretching, ensuring that the mask maintains its shape and performance for a long time without looseness or deformation, and greatly meeting the need of the user.

In this embodiment, the bracket connecting component 4 is a PVC connecting plate 41, and the ice silk fabric layer 31 is connected to the PVC connecting plate 41 through hot press molding. Through the above structure, the PVC connecting plate 41 provides a relatively sturdy structural support for the VR mask, ensuring the shape and stability of the mask main body 1, and contributing to maintaining the appearance of the VR mask, so that the user feels comfortable when wearing the VR mask, and the VR mask is not easily deformed or bent. The ice silk fabric layer 31 and the PVC connecting plate 41 are connected by the hot press molding, which can ensure firm adhesion between the ice silk fabric layer 31 and the PVC connecting plate 41, thereby reducing the risk of separation or falling off of the mask main body 1, improving the durability of a product, and prolonging the life of the product. Moreover, due to the adhesion achieved by hot press molding, a seal is formed between the ice silk fabric layer 31 and the PVC connecting plate 41, which contributes to preventing dust from entering an accommodating cavity between the ice silk fabric layer 31 and the PVC connecting plate 41. This improves the durability and reliability of the product.

In this embodiment, the filling layer 6 includes a first filler 61 and a second filler 62; the first filler 61 is located on one side close to the PVC connecting plate 41; the second filler 62 is located on the other side of the first filler 61 away from the PVC connecting plate 41; the first filler 61 is memory sponge 611; and the second filler 62 is gel 621. The memory sponge 611 and the gel 621 may be bonded by viscidities of their materials. Through the above structure, the memory sponge can adapt to the shape and pressure points of the face of the user to provide a high degree of comfortableness. The memory sponge can reduce a pressure around the eyes and make a wearer feel no discomfort or fatigue. The gel arranged on an upper layer of the memory sponge is closer to the skin of the user. The gel has good temperature adjustment performance and can maintain the temperature of the mask to a certain extent, so that the wearer feels cool and comfortable around the eyes. The mask main body filled with the memory sponge 611 and the gel 621 can greatly improve the comfort of the user when the user wears VR equipment.

In this embodiment, the mask main body 1 is further provided with a connecting piece 7 connected to the mask bracket 2; the mask bracket 2 is provided with a connecting matching member 8; the connecting piece 7 is located on a lower surface of the PVC connecting plate 41; the connecting matching member 8 is located on an upper surface of an inner side of the mask bracket 2; the connecting piece 7 is a flannel layer 71, and the flannel layer 71 is connected to the PVC connecting plate 41 through an adhesive or by hot melting; and the connecting matching member 8 is a hook surface of a hook-and-loop fastener. Through the above structure, the mask main body 1 is connected to the mask bracket 2 through the hook-and-loop fastener. The hook-and-loop fastener is a simple and effective connection method, so that the user can easily detachably connect the mask main body 1 to the mask bracket 2. Furthermore, the hook-and-loop fastener usually has a long service life, can be connected and disconnected for multiple times, and is not easy to wear or damage. Moreover, as a loop surface of the hook-and-loop fastener uses the flannel layer 71, and fluff has a certain degree of adhesion, the loop surface can be better adhered to the corresponding hook surface of the hook-and-loop fastener, ensuring firm connection between the mask main body 1 and the mask bracket 2. As the flannel layer 71 and the PVC connecting plate 41 are connected through the adhesive or by hot melting, the risk of separation is lowered, the reliability of connection is ensured, and loosening or falling off of the mask main body 1 and the mask bracket 2 during use is prevented. This design also makes it easier for the user to clean the mask main body 1. The user can separate the mask main body 1 and clean it separately to maintain hygiene and cleanliness.

In this embodiment, a height of the memory sponge 611 is 14-16 mm; a height of the gel 621 is 2.5-3.5 mm; and a width of the mask bracket 2 is 165 mm. Through the above structure, the appropriate heights of both the memory sponge 611 and the gel 621 can provide greater buffering and support, so that the user feels more comfortable when wearing the VR mask, and the discomfort and fatigue in the eyes are reduced. The width design of the mask bracket 2 can adapt to the shape of the face of the user, ensuring good fitting of the mask and preventing the mask from sliding or falling off.

Referring to FIG. 1 to FIG. 5, a VR mask and mask bracket 2 includes a mask bracket 2, wherein the mask bracket 2 is provided with a viewing port 21; and a mask main body 1, wherein the mask main body 1 is configured to be connected with the mask bracket 2; the mask main body 1 is arranged around the viewing port 21; the mask main body 1 includes a fabric layer 3 and a bracket connecting component 4; the fabric layer 3 is connected to the bracket connecting component 4 to form an accommodating cavity 5; and a filling layer 6 is arranged in the accommodating cavity 5. Through the above structure, when a user wears VR equipment, the fabric layer 3 of the mask main body 1 is in direct contact with the skin of the user. A fabric used in the fabric layer 3 is softer and more comfortable than a hard or viscous material, which can better adapt to the facial contour of the user. Furthermore, the fabric usually has good breathability, which allows air circulation, reduces moisture and excessive sweating, and can satisfy the best performance and improve the wearing experience of the user.

In this embodiment, the fabric layer 3 is an ice silk fabric layer 31. The ice silk fabric layer 31 is an elastic flexible fabric layer 3; and the ice silk fabric layer 31 includes at least one of a polyester fiber, a viscose fiber, polyester or spandex, chinlon or modal, or a cotton blended material. Through the above structure, an ice silk fabric is known for its cool and comfortable tactile impression. It has the characteristics of moisture absorption and heat dissipation and can effectively keep the skin dry, reduce discomfort and sweating, help air circulation, reduce heat accumulation and moisture. This is very important for a user who wears the VR equipment for a long time, and provides better comfort and freshness for the user. Furthermore, due to its elasticity, the elastic ice silk fabric can better adapt to the facial contour of the user, so as to provide a better-fitted wearing experience, so that the mask can uniformly abut against the face and reduce discomfort, pressure points, and friction. Moreover, the elastic ice silk fabric has a recovery capability, which can be recovered to an original shape quickly after stretching, ensuring that the mask maintains its shape and performance for a long time without looseness or deformation, and greatly meeting the need of the user.

In this embodiment, the bracket connecting component 4 is a PVC connecting plate 41, and the ice silk fabric layer 31 is connected to the PVC connecting plate 41 through hot press molding. Through the above structure, the PVC connecting plate 41 provides a relatively sturdy structural support for the VR mask, ensuring the shape and stability of the mask main body, and contributing to maintaining the appearance of the VR mask, so that the user feels comfortable when wearing the VR mask, and the VR mask is not easily deformed or bent. The ice silk fabric layer 31 and the PVC connecting plate 41 are connected by the hot press molding, which can ensure firm adhesion between the ice silk fabric layer 31 and the PVC connecting plate 41, thereby reducing the risk of separation or falling off of the mask main body 1, improving the durability of a product, and prolonging the life of the product. Moreover, due to the adhesion achieved by hot press molding, a seal is formed between the ice silk fabric layer 31 and the PVC connecting plate 41, which contributes to preventing dust from entering an accommodating cavity between the ice silk fabric layer 31 and the PVC connecting plate 41. This improves the durability and reliability of the product.

In this embodiment, the filling layer 6 includes a first filler 61 and a second filler 62; the first filler 61 is located on one side close to the PVC connecting plate 41; the second filler 62 is located on the other side of the first filler 61 away from the PVC connecting plate 41; the first filler 61 is memory sponge 611; and the second filler 62 is gel 621. Through the above structure, the memory sponge can adapt to the shape and pressure points of the face of the user to provide a high degree of comfortableness. The memory sponge can reduce a pressure around the eyes and make a wearer feel no discomfort or fatigue. The gel arranged on an upper layer of the memory sponge can be closer to the skin of the user. The gel has good temperature adjustment performance and can maintain the temperature of the mask to a certain extent, so that the wearer feels cool and comfortable around the eyes. The mask main body filled with the memory sponge and the gel can greatly improve the comfort of the user when the user wears VR equipment.

In this embodiment, the mask main body 1 is further provided with a connecting piece 7; the mask bracket 2 is provided with a connecting matching member 8; the connecting piece 7 is located on a lower surface of the PVC connecting plate 41; the connecting matching member 8 is located on an upper surface of an inner side of the mask bracket 2; the connecting piece 7 is a flannel layer 71, and the flannel layer 71 is connected to the PVC connecting plate 41 through an adhesive or by hot melting; and the connecting matching member 8 is a hook surface of a hook-and-loop fastener. Through the above structure, the mask main body 1 is connected to the mask bracket 2 through the hook-and-loop fastener. The hook-and-loop fastener is a simple and effective connection method, so that the user can easily detachably connect the mask main body 1 to the mask bracket 2. Furthermore, the hook-and-loop fastener usually has a long service life, can be connected and disconnected for multiple times, and is not easy to wear or damage. Moreover, as a loop surface of the hook-and-loop fastener uses the flannel layer, and fluff has a certain degree of adhesion, the loop surface can be better adhered to the corresponding hook surface of the hook-and-loop fastener, ensuring firm connection between the mask main body 1 and the mask bracket 2. As the flannel layer 71 and the PVC connecting plate 41 are connected through the adhesive or by hot melting, the risk of separation is lowered, the reliability of connection is ensured, and loosening or falling off of the mask main body 1 and the mask bracket 2 during use is prevented. This design also makes it easier for the user to clean the mask main body. The user can separate the mask main body 1 and clean it separately to maintain hygiene and cleanliness.

In this embodiment, a height of the memory sponge 611 is 14-16 mm; a height of the gel 621 is 2.5-3.5 mm; and a width of the mask bracket 2 is 165 mm. Through the above structure, the appropriate heights of both the memory sponge 611 and the gel 621 can provide greater buffering and support, so that the user feels more comfortable when wearing the VR mask, and the discomfort and fatigue in the eyes are reduced. The width design of the mask bracket 2 can adapt to the shape of the face of the user, ensuring good fitting of the mask and preventing the mask from sliding or falling off.

One or more implementation modes are provided above in combination with specific contents, and it is not deemed that the specific implementation of the present disclosure is limited to these specifications. Any technical deductions or replacements approximate or similar to the method and structure of the present disclosure or made under the concept of the present disclosure shall fall within the scope of protection of the present disclosure.

What is claimed is:

1. A VR mask and mask bracket, comprising:
   a mask bracket, wherein the mask bracket is provided with a viewing port;
   a mask main body, wherein the mask main body is configured to be connected with the mask bracket; the mask main body is arranged around the viewing port; the mask main body comprises a fabric layer and a bracket connecting component; the fabric layer is connected to the bracket connecting component to form an accommodating cavity; and a filling layer is arranged in the accommodating cavity;
   wherein the bracket connecting component is a PVC connecting plate;
   wherein the mask main body is further provided with a connecting piece, and the mask bracket is provided with a connecting matching member;
   wherein the connecting piece is located on a lower surface of the PVC connecting plate; the connecting matching member is located on an upper surface of an inner side of the mask bracket; the connecting piece is a flannel layer, and the flannel layer is connected to the PVC connecting plate through an adhesive or by hot melting; and the connecting matching member is a hook surface of a hook-and-loop fastener.

2. The VR mask and mask bracket according to claim 1, wherein the fabric layer is an ice silk fabric layer.

3. The VR mask and mask bracket according to claim 2, wherein the ice silk fabric layer is an elastic flexible fabric layer; the ice silk fabric layer comprises at least one of a polyester fiber, a viscose fiber, polyester or spandex, chinlon or modal, or a cotton blended material.

4. The VR mask and mask bracket according to claim 1, wherein the ice silk fabric layer is connected to the PVC connecting plate through hot press molding.

5. The VR mask and mask bracket according to claim 4, wherein the filling layer comprises a first filler and a second filler; the first filler is located on one side close to the PVC connecting plate; the second filler is located on the other side of the first filler away from the PVC connecting plate; the first filler is memory sponge; and the second filler is gel.

6. The VR mask and mask bracket according to claim 5, wherein a height of the memory sponge is 14-16 mm; a height of the gel is 2.5-3.5 mm; and a width of the mask bracket is 165 mm.

* * * * *